(12) United States Patent
Croizat et al.

(10) Patent No.: US 10,500,103 B2
(45) Date of Patent: Dec. 10, 2019

(54) ABDOMINAL WOUND DRESSING WITH APPLICATION AID

(75) Inventors: Pierre Croizat, Herbrechtingen (DE); Axel Eckstein, Heidenheim (DE); Cornelia Wolf, Herbrechtingen (DE)

(73) Assignee: Paul Hartmann AG, Heidenheim (DE)

(*) Notice: Subject to any disclaimer, the term of this patent is extended or adjusted under 35 U.S.C. 154(b) by 329 days.

(21) Appl. No.: 13/605,323

(22) Filed: Sep. 6, 2012

(65) Prior Publication Data

US 2013/0245527 A1 Sep. 19, 2013

Related U.S. Application Data

(60) Provisional application No. 61/533,445, filed on Sep. 12, 2011.

(30) Foreign Application Priority Data

Sep. 9, 2011 (EP) .................................. 11007377

(51) Int. Cl.
| | | |
|---|---|---|
| A61F 13/00 | (2006.01) | |
| A61F 13/14 | (2006.01) | |
| A61M 1/00 | (2006.01) | |
| A61F 13/02 | (2006.01) | |

(52) U.S. Cl.
CPC ...... *A61F 13/148* (2013.01); *A61F 13/00068* (2013.01); *A61F 13/0216* (2013.01); *A61M 1/0088* (2013.01)

(58) Field of Classification Search
CPC ................ A61F 13/148; A61F 13/0216; A61F 13/00068; A61F 13/0203; A61F 13/04; A61F 13/00; A61F 13/00004; A61F 13/00029; A61F 13/02; A61M 1/0088

USPC .............. 602/43, 41, 53, 52, 42, 46, 47
See application file for complete search history.

(56) References Cited

U.S. PATENT DOCUMENTS

| | | | |
|---|---|---|---|
| 5,634,931 A | 6/1997 | Kugel | |
| 5,824,352 A | 10/1998 | Yang et al. | |
| 5,919,180 A * | 7/1999 | Raimondo | ............ A61F 13/141 |
| | | | 128/888 |
| 6,551,356 B2 | 4/2003 | Rousseau | |
| 6,790,213 B2 | 9/2004 | Cherok et al. | |
| 7,825,289 B2 * | 11/2010 | Vess | ..................... A61M 1/0088 |
| | | | 424/445 |
| 8,710,289 B2 * | 4/2014 | Russell et al. | ................... 602/41 |
| 8,853,486 B2 | 10/2014 | Wild et al. | |

(Continued)

FOREIGN PATENT DOCUMENTS

| | | |
|---|---|---|
| RU | 2150387 C1 | 6/2000 |
| RU | 2240763 C2 | 11/2004 |

(Continued)

*Primary Examiner* — Victoria J Hicks
(74) *Attorney, Agent, or Firm* — Dilworth & Barrese, LLP

(57) ABSTRACT

The invention relates to a wound dressing and to a device for use in negative-pressure wound therapy, in particular for wounds in the abdominal region, and also to methods for producing the device. The wound dressing includes at least one flexible film for application onto the wound bed, more particularly onto exposed internal organs or onto the greater omentum, and furthermore at least one pocket, which is present on the side of the wound dressing that faces away from the wound during use and which simplifies the uniform application and placement of the wound dressing on the wound bed.

21 Claims, 8 Drawing Sheets

(56) References Cited

U.S. PATENT DOCUMENTS

| | | |
|---|---|---|
| 8,926,574 B2 | 1/2015 | Croizat et al. |
| 9,492,327 B2 | 11/2016 | Heaton et al. |
| 2002/0146955 A1* | 10/2002 | Levine ................ A61F 13/0203 442/328 |
| 2004/0064132 A1* | 4/2004 | Boehringer .......... A61M 1/0011 604/543 |
| 2006/0241541 A1* | 10/2006 | Ravikumar ..................... 602/46 |
| 2009/0099519 A1 | 4/2009 | Kaplan |
| 2010/0063484 A1 | 3/2010 | Heagle |
| 2011/0144599 A1 | 6/2011 | Croizat et al. |

FOREIGN PATENT DOCUMENTS

| | | |
|---|---|---|
| WO | 1993/009727 A1 | 5/1993 |
| WO | 1996/009795 A1 | 4/1996 |
| WO | 2001/085248 A1 | 11/2001 |
| WO | 2002/074199 A1 | 9/2002 |
| WO | 2003/059201 A1 | 7/2003 |
| WO | 2010/016791 A1 | 2/2010 |
| WO | 2010/051068 A1 | 5/2010 |
| WO | 2010/124844 A1 | 11/2010 |
| WO | 2010124844 A1 | 11/2010 |
| WO | 2011018132 A1 | 2/2011 |
| WO | 2011018133 A1 | 2/2011 |
| WO | 2011076340 A1 | 6/2011 |
| WO | 2011091947 A1 | 8/2011 |
| WO | 2011091952 A1 | 8/2011 |
| WO | 2012/069167 A1 | 5/2012 |

* cited by examiner

ABDOMINAL WOUND DRESSING WITH APPLICATION AID

CROSS REFERENCE TO RELATED APPLICATIONS

This application claims priority to U.S. Provisional Application No. 61/533,445 filed Sep. 12, 2011, which is herein incorporated by reference.

BACKGROUND

Field of the Invention

The present invention relates to a wound dressing and to a device for use in negative-pressure wound therapy, in particular for wounds in the abdominal region, and also to methods for producing the device. The invention furthermore relates to a surgical instrument for applying a wound dressing.

Background of the Art

Devices for negative-pressure wound therapy and wound dressings as components of such devices are known from the prior art.

Thus, for example, WO1993/009727 describes a device for promoting wound healing by the application of negative pressure to the region of skin having the wound and surrounding the wound. The device as per WO1993/009727 comprises a vacuum apparatus for producing the negative pressure, an airtight cover of the wound referred to as sealing apparatus, which is functionally connected to the vacuum apparatus, and also a wound dressing referred to as screen apparatus for positioning on the wound within the sealing apparatus. The screen apparatus is a porous polymer foam, for example polyester foam. According to the description of WO1993/009727, the wound healing of different types of wounds, such as burn wounds, pressure sores or lacerations, can be accelerated by the application of negative-pressure therapy.

Here, the term "negative pressure" refers to an air pressure within the wound bandage that is reduced compared to the ambient air pressure (atmospheric air pressure). "Within the wound bandage" is understood to mean the interspace (wound space) formed by the airtight cover material and the body tissue in the wound region. "Negative pressure" is often also referred to as "low pressure". In the context of the invention, the pressure difference between the air pressure within the wound bandage and the ambient air pressure is specified in mm Hg (millimeters of mercury) because this is conventional in the field of negative-pressure therapy. 1 mm Hg corresponds to one Torr or 133.322 Pa (pascal). In the context of the invention, the negative pressure, i.e. the pressure difference between the air pressure within the wound bandage and the ambient air pressure, is specified as a positive number in mm Hg.

Particularly large-area wounds can be created in the abdominal region, either as a result of injury or as a result of surgical interventions. By way of example, surgical interventions in the abdominal region are undertaken in the case of surgical treatment of acute and life-threatening diseases of the abdominal cavity. Within the scope of post-operative care of such surgical interventions, it may also be necessary to cover the open abdominal region only temporarily by means of a temporary wound closure.

In the case of an abdominal wound, exposed internal organs or the greater omentum (also referred to as omentum majus or great omentum) form a wound bed, i.e. a body surface situated within a wound edge. When tending an abdominal wound, a layer of the wound dressing oriented toward the wound (said layer is referred to as wound contact layer below) is directly applied to exposed internal organs or to the greater omentum. The wound contact layer lying on the exposed internal organs or on the greater omentum also serves as an organ screening layer during the negative-pressure treatment of an abdominal wound and should prevent organs or the greater omentum from inadvertently adhering to the abdominal wall. The edge region of the wound dressing is usually inserted into the interspace formed by the abdominal wall and internal organs.

During the treatment of a wound on the open abdomen, it may be necessary to drain a very large amount of liquid, for example more than 5 l within 48 hours. By way of example, very large amounts of liquid to be drained can be created during the surgical treatment of a bowel obstruction (ileus) or an inflammation of the peritoneum (peritonitis).

WO01/85248 has disclosed a bandage for temporarily covering wounds from accidents or surgical interventions, more particularly abdominal wounds. The bandage is provided for use in negative-pressure therapy. WO01/85248 proposes to cover the wound bed with a film provided with holes. A porous foam is applied to the film which constitutes the wound contact layer. On the side that faces away from the wound, the bandage comprises a cover film which is impermeable to liquids and has an adhesive edge for sealing the wound region in an airtight fashion. Furthermore, provision is made for connection means which extend through the cover film as far as the porous foam in order to be able to connect the wound space to a negative-pressure source. During operation, wound exudate can be removed from the wound space by virtue of the liquid first of all reaching the porous foam through the openings in the perforated film and furthermore reaching the connection means via the foam, said connection means being in direct contact with the porous foam.

WO01/85248 is directed, in particular, to a wound bandage that can be replaced without damage to or traumatization of the wound. Such damage when the bandage is changed can occur if the wound bandage adheres during the therapy to the tissue situated therebelow or if tissue grows into the bandage, in particular if fibrous tissue grows into the foam portion of the wound bandage. WO01/85248 wishes to reduce the undesired growth of tissue into the bandage by virtue of reducing the direct contact between porous material and wound bed. In this respect, WO01/85248 proposes that the area of the openings in the film provided with holes is less than 10% of the effective area of the film. Ideally, the open area should be less than 1 or 2% of the area of the film. According to WO01/85248, the openings in the film can be present in the form of slits, which further reduces the contact between foam and wound bed.

WO2010/051068 describes a wound dressing for the open abdomen, the former comprising a multiplicity of enveloped strand-like pressure distribution elements which are functionally coupled by a central connection element. A further pressure distribution element is applied to the side of the central connection element that faces away from the wound. By way of example, the pressure distribution elements can be an open-cell foam. The wound dressing can be cut to size.

US2009/0099519 describes an abdominal bandage for negative-pressure therapy, which comprises an enveloped cushion and a heater element for controlling the temperature.

WO2010/124844 discloses a wound dressing which, in particular, is provided for use on the open abdomen. The wound dressing comprises two web-like elements, which form a drainage space situated between their inner delimiting surfaces. At least one of the web-like elements can have openings, with provision in particular being made for canal-shaped openings that open into the drainage space and can promote capillary action.

The patent application DE102010052336.4 (not yet published at the time of the present application) by the applicant of the present patent application describes a bandage for use in negative-pressure wound therapy, in particular for wounds in the abdominal region, comprising a flexible film as wound contact layer and at least one conduit applied to the film, made of a flexible elastomeric material with a thickness (H) of at most 30 mm. The conduit has at least one continuous cavity. Both conduit and film have a multiplicity of openings, and so a fluid connection can be established between the conduit and the wound space. The lateral openings present in the conduit in addition to the openings situated at the ends enable wound fluid to be taken up into the continuous cavity. On the side that faces away from the wound during use, the wound dressing can have at least one or more pockets, situated toward the edge and open toward the center of the wound dressing, with a depth of at most 6 cm, which pockets simplify the uniform application and laying out of the wound dressing on the wound bed.

When applying an abdominal wound dressing to exposed internal organs or the greater omentum, the user, e.g. a surgeon, must take care that there is even application of the bandage on the wound bed. In particular, the user may find it difficult to apply the encircling edge region of the wound dressing between abdominal wall and internal organs.

SUMMARY

The present invention is based on the object of providing an improved abdominal wound dressing for negative-pressure therapy. In particular, it is an object of the present invention to provide an abdominal wound dressing that is improved in respect of user friendliness. Accordingly, it should be easy to apply the wound dressing, match it to the conditions of the individual wound well and replace it without adhesion or growth into the bed. The wound dressing should furthermore have a sufficient drainage capacity.

According to the invention, this object is achieved by a wound dressing for use in negative-pressure wound therapy, in particular for treatment of abdominal wounds, according to claim 1. The wound dressing comprises a first flexible film with a first and a second side, with the first side being provided for application on the wound bed, more particularly on exposed internal organs or on the greater omentum. The first flexible film has at least one opening in order to enable fluid communication through the film. Moreover, the wound dressing comprises at least one pocket that is open predominantly toward the center of the wound dressing, simplifying the uniform application and laying out of the wound dressing on the wound bed. The at least one pocket is preferably situated toward the edge. The depth of the pocket is preferably at most 15 cm, more particularly at most 10 cm. The pocket is preferably formed by the application of cone-like or areally designed material sections, more particularly pieces of film, or by folding back a film section comprised by the wound dressing. According to the invention, there is no conduit present which is applied to the second side of the first film, made of a flexible elastomeric material with a thickness (H) of at most 30 mm and has a continuous cavity, wherein "thickness (H)" in this case should be understood as illustrated in the patent application DE102010052336.4 (not yet published at the time of the present application).

During the application in negative-pressure wound therapy, the wound dressing can be connected in a fluid-conducting fashion to a negative-pressure source such that fluid communication can be established between the negative-pressure source and the wound space. The cover film is usually attached to the region of the skin surrounding the wound in a sealing fashion. In this context, a fluid is understood to mean both liquids (e.g. wound fluid, blood, intestinal fluid or rinsing fluid) and also gases (e.g. air or carbon dioxide).

According to the invention, it is proposed to provide a wound dressing with at least one pocket, as a result of which the application of the wound dressing by a user can be substantially simplified. In particular, the edge of the wound dressing according to the invention can be applied more easily and without folds into the interspace formed by internal organs or greater omentum and abdominal wall. To this end, the user can insert a flat surgical instrument, e.g. a stomach and intestinal spatula, into the pocket and thereupon carefully insert the wound dressing, which is temporarily held on the spatula by the pocket, under the abdominal wall. After the edge region of the wound dressing has been inserted under the abdominal wall, the spatula is once again pulled out of the pocket. The wound dressing preferably comprises a multiplicity of pockets. It is then possible— successively or simultaneously—to insert a plurality of peripheral portions of the wound dressing under the abdominal wall provided that provision is made on the wound dressing for appropriately arranged pockets.

Instead of an instrument, the user can also insert one or more fingers into the at least one pocket for applying the wound dressing.

The at least one pocket applied to the wound dressing can even simplify the application of a large-area wound dressing in those cases in which there is no intention of inserting an edge region of the wound dressing under the abdominal wall, and so there are further options for using the wound dressing according to the invention. Thus, it was found that pockets applied to the wound dressing allow particularly careful matching of the wound dressing to the body surface which is referred to as wound bed herein.

The wound dressing according to the invention comprises a first flexible film with a first and a second side, with the first side being provided for application on the wound bed. During use, the first side of the flexible film is placed into direct contact with the surface referred to here as wound bed, i.e. more particularly onto the internal organs or the greater omentum exposed during surgery or as a result of injury. In the case of an abdominal wound, the edge region of the wound dressing is usually inserted into the interspace formed by wound bed and abdominal wall. A wound dressing applied thus serves as an organ screening layer, particularly in the case of a temporary wound closure, and should moreover prevent adhesive bonding between abdominal wall and the wound bed. It is therefore essential for the first flexible film to consist of a material which does not adhere to or grow together with the wound bed or the abdominal wall for the duration of the application. The material should have atraumatic properties.

Suitable materials for the first flexible film comprise thermoplastic films, more particularly films made of ethylene-vinyl acetate (abbreviated EVA below), polyurethane (abbreviated PU below), polyethylene (abbreviated PE below), polyethylene terephthalate (abbreviated PET below), PTFE (referred to as polytetrafluoroethylene below), polyvinyl chloride (abbreviated PVC below), thermoplastic elastomers (abbreviated TPE below), polyorganosiloxane (shortened to silicone below) or a mixture thereof. In this context, the label TPE comprises thermoplastic elastomers based on olefins (TPO), cross-linked thermoplastic elastomers based on olefins (TPV), thermoplastic elastomers based on urethane (TPU), thermoplastic polyester elastomers or thermoplastic copolyesters (TPC), styrene block copolymers (TPS) and thermoplastic copolyamides (TPA). The thermoplastic film is preferably a PE film.

The mass per unit area of the first flexible film is preferably at least 30 g/m$^2$ and at most 150 g/m$^2$, more particularly at least 45 g/m$^2$ and at most 95 g/m$^2$ and particularly preferably at least 55 g/m$^2$ and at most 65 g/m$^2$.

According to a particularly preferred embodiment, the first flexible film is a support film-free PE film with a mass per unit area of 55 g/m$^2$ to 65 g/m$^2$, with the mass per unit area being determined pursuant to the norm EN ISO 2286-2, for example the products "Folie MEDIFOL® 3D, Type 44600" or "Folie MEDIFOL® 3D T16, Type 44601 T16" by rkw Prolife (Wasserburg, Germany).

The first flexible film has at least one opening in order to enable negative-pressure communication with the whole wound space and to ensure unhindered drainage of fluid.

According to a first embodiment, the opening is a centrally arranged opening with a diameter of, for example, between 0.5 cm and 5.0 cm.

According to an embodiment which is preferred according to the invention, the first flexible film has a multiplicity of openings distributed over the area, which openings ensure a passage of wound fluid through the film and an even distribution of the negative pressure in the wound space. The openings can be holes or slits. In this context, a hole refers to an opening which, in a plan view and in the non-stretched state, has an open area. In this context, a slit refers to an opening which, in a plan view and in the non-stretched state, has no open area. The desired permeability of the film in respect of wound fluid can be set in suitable fashion by the shape and dimension of the openings. Round, oval, polygonal or e.g. star-shaped holes are feasible. By way of example, the slits can be elongate or cross-shaped slits.

The openings can be present distributed in a regular, i.e. in regularly repeating patterns, or random fashion across the area of the first film.

In the process, it is also possible for only a first portion of the first flexible film to have a multiplicity of openings distributed across the area while a further portion of the first flexible film has no openings. Thus, for example, it can be advantageous for a central portion of the first film to have a multiplicity of openings while a peripheral portion of the film has no openings. A reverse arrangement is likewise possible.

Should the openings be slits, these should respectively have a length of at least 1 mm and at most 30 mm, preferably at least 2 mm and at most 20 mm, and more particularly at least 5 mm and at most 10 mm. In this case it was found that a film which has slits with a length of at least 5 mm and at most 10 mm, with between 10 and 90 of such slits being introduced on a film area of 100 cm$^2$, has particularly advantageous properties in respect of stability and at the same time has sufficient fluid permeability.

The flexible film preferably has a multiplicity of openings, with the openings being holes. The diameter of the holes can be adjusted in suitable fashion in respect of the desired fluid permeability, for example in a range between 0.1 mm and 5 mm in the case of circular holes. Ranges between at least 0.2 mm and at most 0.4 mm are particularly preferred in this case in respect of an expedient combination of fluid permeability and atraumatic properties of the film. In this case, holes with a diameter of 0.3 mm have particularly advantageous properties.

If the openings in the first film are holes, the sum of the open area of the holes should moreover be at least 0.5%, but preferably at least 10%, of the areal extent of the film in order to ensure sufficient permeability of the film for wound fluid. In the process, an open area of 25% of the film should, where possible, not be exceeded because this could otherwise have a negative effect on the stability of the film. Hence it is preferable for the sum of the open area of the holes present in the film to be at least 0.5% and at most 25% of the areal extent, preferably at least 12% and at most 23% of the areal extent.

Fluid permeability, stability and the tendency of tissue to grow into the film are influenced by the open area of the film.

According to a preferred embodiment of the invention, the open area of the holes present in the first film is at least 13% and at most 15% of the areal extent of the film. Such a film is found to be advantageous, particularly in respect of fluid permeability, atraumatic properties and stability. In this embodiment, the number of the openings present in the first film per unit area should be at least 150 per cm$^2$ and at most 190 per cm$^2$, more particularly at least 165 per cm$^2$ and at most 171 per cm$^2$.

According to a further preferred embodiment of the invention, the open area of the holes present in the first film is at least 20% and at most 22% of the areal extent of the film. Such a film has a high fluid permeability and flexibility or softness. In this further embodiment, the number of the openings present in the first film per unit area should be at least 260 per cm$^2$ and at most 300 per cm$^2$, more particularly at least 275 per cm$^2$ and at most 285 per cm$^2$.

It is also feasible for the film to have a multiplicity of openings distributed across the area, with the openings being a combination of holes and slits. By way of example, this can be embodied such that a specific surface region of the film has holes and another surface region of the first film has slits.

The invention comprises further variants, not specifically mentioned here, in respect of shape, dimension, number and arrangement of the openings in the first flexible film.

According to a particularly preferred embodiment of the invention, the openings present in the first film are created by perforating or stamping the film such that openings are created which, to the greatest possible extent, have a conical or cylindrical form. The openings therefore have a three-dimensional structure such that the film has a smooth side and a roughened side situated opposite to the smooth side. By way of example, openings with a three-dimensional structure can be introduced by means of a stamping roller. Alternatively, openings with a three-dimensional structure can already be created during the production of the film, for example by guiding the extruded, still molten film over a rotating, low-pressure perforated roller.

Particular advantages when using a film with such three-dimensionally structured openings for the wound dressing according to the invention emerge in particular if the first side of the first film, provided for application on the wound bed, is formed by the smooth side of the film and the second side of the first film is formed by the roughened side of the film. The smooth side of the film, provided for application to the wound bed, has a low tendency to adhere to the wound bed. Secondly, the three-dimensionally structured openings bring about a spacing of the wound bed to further plies of the bandage, e.g. to a foam ply, if such additional bandage layers are present. A spacing from further plies can reduce undesirable growing of fibrous tissue into further bandage plies.

Films that have conically or cylindrically shaped openings are commercially available, e.g. the aforementioned films with the names "Folie MEDIFOL® 3D, Type 44600" or "Folie MEDIFOL® 3D T16, Type 44601 T16" (produced by rkw ProLife, Wasserburg, Germany).

According to a very advantageous development of the invention, the wound dressing furthermore comprises a second flexible film, with at least a portion of the area of the first side of the second film being applied to the second side of the first film that faces away from the wound during use. The second film is usually brought into contact with the first film over the whole area. However, as explained in more detail below, provision can be made for material pieces to be introduced into the interspace formed by the first film and the second film such that only portions of the area of the second film are in direct contact with the first film.

The second film is preferably made of a material that is fluid-impermeable to the greatest possible extent. In order to produce the second flexible film, use can in particular be made of the materials and finished products already mentioned above in the context of the first flexible film, for example thermoplastic films, more particularly films made of EVA, PU, PE, PET, PTFE, PVC, TPE, silicone or a mixture thereof.

A wound dressing formed from two film plies can have advantageous properties in respect of stability and manageability of the wound dressing. The permeability of the wound dressing for wound fluid and the atraumatic properties of the wound dressing can be matched to the therapeutic requirements by a suitable selection of first film and second film.

The second film is attached in a non-detachable fashion to the second side of the first film, for example by adhesive bonding, pressing or welding. The attachment can be brought about over an area, in line-form or in punctiform fashion (adhesion points). By way of example, adhesive bonding can be brought about by the application of an adhesive or by means of a sticky tape. By way of example, welding can be brought about by heat or ultrasound.

According to a particularly advantageous embodiment, the second film is attached to the first film by punctiform adhesive bonding or welding of the films, with provision being made for a multiplicity of adhesion points distributed across the area. In the case of such a connection between first and second film, a fluid-conducting interspace (labyrinth) is created between first and second film, which can promote the drainage of wound exudate in an advantageous fashion.

According to an advantageous embodiment, the second film is embodied to be impermeable to fluid to the greatest possible extent and merely has a single opening. At the same time, the first flexible film should have a multiplicity of openings distributed over the area such that wound fluid can reach the interspace formed by the first film and the second film through the openings in the first film. The fluid can then be conducted on from the interspace to the negative-pressure source via an opening preferably arranged in the central region of the second film.

According to a further particularly advantageous embodiment, the first film and the second film have a multiplicity of openings, which are suitable for passing fluid through them, distributed over the area, wherein the open area of the holes present in the first film and in the second film should respectively be at least 0.5% and at most 25% of the areal extent. In the process, it may be advantageous if the openings present in the first film and the openings present in the second film are arranged such that the openings are not congruent to one another to the greatest possible extent. In this context "not congruent to one another to the greatest possible extent" is understood to mean that openings in the first and second film that are congruent to one another at best result by chance and are only present in small numbers. In particular, at least 90%, preferably 95%, of the openings in the first film should not in the process be congruent to an opening in the second film.

In the context of an embodiment of the wound dressing according to the invention that comprises two or more film plies, it was moreover found to be particularly advantageous to provide between first and second films a cavity which is largely stable, even in the presence of negative pressure. Such a largely stable cavity can be created by virtue of bringing first and second film onto one another at a distance from one another. By way of example, this can be brought about by the introduction of suitable pieces of material between the films. In the simplest case, the piece of material can be a simple spacer, for example pimples made of plastic. Pieces of material that have fluid-conducting properties, e.g. pieces of material made of foam, are also feasible. Spacing the film layers while forming a cavity can also be achieved by the use of a film material which has three-dimensionally shaped openings. To this end, the films must be placed onto one another such that the three-dimensional structures are present facing one another.

In this context, reference is made to the content of the already cited patent application WO2010/124844, which describes a wound cover made of two web-shaped elements. The web-shaped elements have funnel-shaped perforations and form a drainage space situated between their inner boundary areas, with a capillary effect occurring. Here, two webs with funnel openings facing one another can be placed over one another and interconnected in a punctiform fashion. Accordingly, as per a further advantageous embodiment of the invention, it is proposed to apply onto the wound cover disclosed in WO 2010/124844 at least one pocket that is predominantly open toward the center of the wound dressing onto the side of the wound dressing that faces away from the wound during use.

The aforementioned embodiment of the invention therefore relates to a wound dressing for use in negative-pressure wound therapy, in particular for the treatment of abdominal wounds, comprising i) a first flexible film with a first and a second side, with the first side being provided for application on the wound bed, more particularly on exposed internal organs or on the greater omentum, and with the first film furthermore having a multiplicity of openings, which, to the greatest possible extent, have a conical or cylindrical shape and have a three-dimensional shape, distributed across the area, ii) a second flexible film with a first and a second side, with the first side of the second film being applied to the second side of the first film and with the second film furthermore having a multiplicity of openings, which, to the greatest possible extent, have a conical or cylindrical shape, distributed across the area, and iii) at least one pocket, preferably a plurality of pockets, which is/are predominantly open toward the center of the wound dressing, is/are present on the side of the wound dressing that faces away from the wound during use and simplifies/simplify the uniform application and placement of the wound dressing on the wound bed. The depth of the at least one pocket is preferably at most 15 cm, more particularly at most 10 cm.

Here, the first and second film should be applied onto one another such that the three-dimensional structures are present facing one another and a drainage space is formed situated between their inner boundary areas.

Furthermore, the wound dressing is characterized in that there is no conduit present which is applied to the second side of the first film, made of a flexible elastomeric material with a thickness (H) of at most 30 mm and has a continuous cavity.

Here, the at least one pocket can in particular comprise a material section embodied in a cone-like fashion or an areal material section.

Developing this thought further, it is also possible to arrange a fluid-conducting material, e.g. a foam, between first and second film. The already mentioned patent application WO2010/051068, to the content of which reference is made herewith, describes an abdominal wound dressing embodied thus. The wound dressing in WO2010/051068 comprises a multiplicity of enveloped strand-like pressure-distribution elements which can, for example, consist of an open-cell foam. The pressure-distribution elements are applied to a first film, which is provided for contact with the body tissue. The pressure-distribution elements are enveloped by a further second film ply on the lateral side and on the wound-distant side. The second film is connected in a non-detachable fashion to the first film in the sections of the wound dressing localized between the strands. First and second films have openings.

In this context, reference is furthermore made to the likewise already mentioned patent application WO01/85248. WO01/85248 proposes to cover the wound bed with a film provided with holes, onto which a porous foam is applied. On the wound-distant side, the porous foam is covered by a further film ply with openings such that the foam is held in an interspace formed by the first and second film. The film plies are interconnected on the lateral side in a non-detachable fashion.

Within the scope of the present invention, the wound dressings described in the patent applications WO2010/051068 and WO01/85248 can be provided with at least one pocket, predominantly open toward the center of the wound dressing, in order to simplify the uniform application and laying out of the wound dressing on the wound bed.

The aforementioned further embodiment of the invention therefore relates to a wound dressing for use in negative-pressure wound therapy, in particular for the treatment of abdominal wounds, comprising i) a first flexible film with a first and a second side, with the first side being provided for application on the wound bed, more particularly on exposed internal organs or on the greater omentum, and with the first film furthermore having a multiplicity of openings distributed across the area, ii) a second flexible film with a first and a second side, with the first side of the second film being applied to the second side of the first film and with the second film furthermore having a multiplicity of openings distributed across the area, iii) at least one piece of material introduced between first film and second film such that a drainage space situated between the inner boundary areas of the films is formed, and iv) at least one pocket, preferably a plurality of pockets, which is/are predominantly open toward the center of the wound dressing, is/are present on the side of the wound dressing that faces away from the wound during use and simplifies/simplify the uniform application and placement of the wound dressing on the wound bed. The depth of the at least one pocket is preferably at most 15 cm, more particularly at most 10 cm. Furthermore, the wound dressing is characterized in that there is no conduit present present which is applied to the second side of the first film, made of a flexible elastomeric material with a thickness (H) of at most 30 mm and has a continuous cavity.

Here, the at least one pocket can in particular comprise a material section embodied in a cone-like fashion or an areal material section. The at least one piece of material introduced between first film and second film preferably is an open-cell foam, in particular an open-cell polyurethane foam. In this case, polyester polyurethanes are particularly preferred, with reference being made in particular to the foam described in the patent application DE 102010034819.8 (not yet published at the time of the present application).

Further film plies arranged on the wound-distant side can optionally be applied to a second flexible film. According to a further advantageous embodiment of the invention, the wound dressing therefore comprises one or more further flexible film plies, wherein the one film ply or the plurality of film plies are provided for application on the side of the wound dressing that faces away from the wound during use.

In order to produce the one or more further flexible film plies, use can in particular be made of the materials and finished products already mentioned above in the context of the first flexible film, for example thermoplastic films, more particularly films made of EVA, PU, PE, PET, PTFE, PVC, TPE, silicone or a mixture thereof. In respect of attaching the one or more further flexible films on the second flexible film, reference is made to the aforementioned suggestions for attaching the second film on the first film.

As a result of using further film plies, the stability and the permeability of the wound dressing for wound fluid can be matched more closely to the therapeutic requirements.

In order to maintain the drainage capacity of the wound dressing over a period of a number of hours, it is proposed in the context of a further advantageous embodiment of the invention to provide the film materials comprised by the wound dressing with a substance with an anticoagulating effect. As a result of this, it is possible, for example, to reduce a blockage of the openings or of the interspace—if present—formed by the first and second film. According to such a particularly advantageous embodiment, the first flexible film and/or the second flexible film (if present) and/or the one or more further flexible film plies (if present) has/have a coating of or impregnation with a substance with an anticoagulating effect (for example Heparin or another substance with anticoagulating effect usually used for coating medical surfaces or tubules). It is likewise feasible to provide the material sections provided for forming a pocket with such a coating or impregnation.

According to the invention, the wound dressing comprises at least one pocket that is open predominantly toward the center of the wound dressing, simplifying the uniform application and laying out of the wound dressing on the wound bed. Here, the at least one pocket is preferably arranged situated toward the edge on the wound dressing. Here, situated toward the edge is understood to mean that the pocket is primarily attached to the peripheral component of the wound dressing. The spacing between the outer edge of the pocket and the edge of the wound dressing could for example be 0 cm to 10 cm on a circular wound dressing with a diameter of 45 cm in the case of an arrangement referred to within this meaning as situated toward the edge. The depth of the at least one pocket is preferably at most 15 cm, more particularly at most 10 cm. The at least one pocket is applied on the side that faces away from the wound during use (wound-distant side) of that film ply that is present facing away from the wound during use: to the extent that the wound dressing merely comprises a first flexible film, the pocket is applied on the second side of the first film. To the extent that the wound dressing merely consists of two film plies, i.e. of a first flexible film and a second flexible film, the pocket is generally applied to the second side of the second film. An exception may occur in this context if the second film only lies over a portion of the area of the first film. In this case it would also be possible to apply the pocket on that portion of the first film that is not covered by the second film. To the extent that the wound dressing comprises one or more further flexible film plies, the pocket is generally applied on the side that faces away from the wound during use of that film ply that is present facing away from the wound during use. This means that the pocket is always provided on the wound-distant side on the wound dressing.

In one embodiment herein the at least one pocket (25) is situated at or adjacent to a peripheral edge of the wound dressing.

Pockets that are suitable within the scope of the invention can be envisaged in a multiplicity of shapes. What is essential in this case is that there is an opening which is predominantly oriented toward the center of the wound dressing and into which the surgical instrument, more particularly a stomach and intestinal spatula, can be inserted or hooked. It is furthermore essential that a side of the pocket opposite to the opening is able to provide support to the inserted or hooked-in surgical instrument. The easiest way of implementing such a support is by a seam lying opposite to the opening of the pocket. The opening of the pocket should predominantly be oriented toward the center of the wound dressing such that a surgical instrument moved outward from the center of the wound dressing can be inserted into the opening and can find support therein.

An opening of the pocket predominantly oriented toward the center of the wound dressing can likewise simplify a manual application of the wound dressing if the user wishes to insert a finger instead of a surgical instrument into the at least one pocket.

In respect of its size and shape, the pocket should be matched to the surgical instrument or optionally to a human finger. By way of example, the pocket can substantially have the shape of a rectangle, a trapezium, a semicircle, a triangle, an annulus or an annular sector, with further shapes being comprised which are not described here in any more detail but emerge for a person skilled in the art from the holding function of the pocket.

The depth a of the pocket, i.e. the spacing of the opening of the pocket, from the opposite edge of the pocket, should preferably be at most 15 cm, more particularly at most 10 cm. The depth a should be at least 0.3 cm, but preferably at least 1 cm, so that the surgical instrument inserted into the pocket or a finger optionally inserted into the pocket cannot slip out of the pocket during the application of the wound dressing. A pocket which is suitable according to the invention therefore preferably has a depth of 1 cm to 10 cm.

In respect of the width b of the pocket, it is likewise necessary to match the former to the surgical instrument that is used when applying the wound dressing, which is why the width b of the pocket must at least equal the width of the instrument because otherwise the latter cannot be inserted into the pocket. However, it is advantageous to design the pocket to be substantially wider than the instrument because it is easier to insert the instrument into the pocket in the case of a pocket designed like this. In this case, the user does not need to take care to find a comparatively narrow opening of the pocket, which may be difficult in the case of a strongly bleeding wound. In general, the width b of the pocket is at least 1 cm, preferably at least 2 cm.

According to the invention, the wound dressing comprises at least one pocket present on the side of the wound dressing that faces away from the wound during use (wound-distant side). However, it proves to be particularly advantageous for the application of the wound dressing if the wound dressing comprises a multiplicity of pockets, which are applied at various points on the wound dressing. In this case, it is proposed that the wound dressing comprises at least 3 pockets, preferably at least 4, more particularly at least 6 pockets. The pockets should be applied to the wound dressing with a spacing between one another that is uniform to the greatest possible extent. In particular, the pockets can be present arranged on one or more concentric circles which encircle the center point of the wound dressing, with the pockets preferably being present on each circle distributed with a uniform spacing between one another. The pockets are preferably present on at least 30% of the circumference of the aforementioned concentric circle, more particularly on at least 50% of the circumference.

The wound dressing according to the invention can be matched without restrictions to the shape and size of the wound by the user, i.e. by the medical practitioner or by the medical staff, for example by simple cutting to size by means of sterile scissors. By contrast, to the extent that it is desired to provide the product matched to predefined wound shapes and wound dimensions already during production, there are likewise no restrictions in this respect as a result of the design of the wound dressing according to the invention. In respect of the possibility of the user cutting the wound dressing to size, it is particularly advantageous here if the pockets are present on the wound dressing arranged on a plurality of concentric circles which encircle the center point of the wound dressing. If the pockets arranged further on the outside are cut off or destroyed during the cutting to size in the case of such an arrangement, it is still possible to use the pockets present further on the inside when applying the wound dressing.

A preferred embodiment of the wound dressing according to the invention comprises at least one pocket, wherein the pocket is formed by the application of areal sections of material, more particularly pieces of film, on the side of the wound dressing that faces away from the wound during use. In particular, the pocket can be attached to the wound dressing by adhesive bonding, thermal welding, pressing or ultrasound welding. The wound dressing is attached at the edge of the material section such that an outer seam is produced. Here, the edge of the material section predominantly oriented toward the center of the wound dressing is not connected to the wound dressing such that there is an opening available for inserting a surgical instrument or a finger. In terms of its design, such a pocket is similar to a shirt pocket, i.e. a pocket sealed on three sides by a seam, which has an opening into which an object can be inserted. Here, the inner surface of the pocket that points toward the wound during use is formed by the film portion of the wound dressing arranged on the wound-distant side, while the inner surface of the pocket that points away from the wound during use is formed by the applied material section. Such a pocket can be produced in a simple and cost-effective manner.

According to an alternative and likewise very advantageous embodiment of the invention, the wound dressing has one or more pockets on the wound-distant side, which pockets are made of a material section in the form of an annulus. A pocket embodied thus is particularly suitable for application to a circular abdominal wound dressing. On its outer circumference, the material section with the shape of an annulus is attached to the wound dressing such that a circular seam is formed. Each material section respectively forms a single pocket, which encircles the center of the wound dressing and has an opening pointing toward the center of the wound dressing. Here, the outer circumference of the annulus may at most have the dimensions of the wound dressing. The inner circumference of the annulus should preferably be selected such that a pocket is formed with a depth of at most 15 cm, more particularly of at most 10 cm. It is possible to apply a plurality of such pockets, arranged concentrically, onto the wound dressing. This simplifies the application of a wound dressing which is fitted to the wound dimension by cutting to size: after destroying a pocket applied further to the outside by cutting to size, a pocket available further to the inside can be used during the application of the wound dressing.

Here the aforementioned embodiment is not restricted to wound dressings with a precise circular design, but rather can likewise be embodied in the case of oval abdominal wound dressings if the material section is suitably adapted.

In the context of a pocket formed by areal material sections, the present invention is directed to a method for producing a wound dressing, comprising the following steps a) provision of a first flexible film with a first and a second side, with the first side being provided for application on the wound bed, more particularly on exposed internal organs or on the greater omentum, and with the film having at least one opening, b) provision of at least one areal material section, more particularly at least one piece of film, and c) application of the at least one areal material section onto the second side of the first film such that at least one pocket is formed which is predominantly open toward the center of the wound dressing.

Here, according to the invention, there is no conduit present which is applied to the second side of the first film, made of a flexible elastomeric material with a thickness (H) of at most 30 mm and has a continuous cavity.

According to an advantageous development of the invention, the wound dressing, as already presented earlier in the text, can comprise a second flexible film. In such a case, the method for producing a wound dressing comprises the a) provision of a first flexible film with a first and a second side, with the first side being provided for application on the wound bed, more particularly on exposed internal organs or on the greater omentum, and with the film having at least one opening, b) provision of a second flexible film with a first and a second side, with the first side being provided for application on the second side of the first film that faces away from the wound during use, c) provision of at least one areal material section, more particularly at least one piece of film, d) application of the first side of the second flexible film onto the second side of the first flexible film, and e) application of the at least one areal material section onto the second side of the second film such that at least one pocket is formed which is predominantly open toward the center of the wound dressing.

Here, according to the invention, there is no conduit present which is applied to the second side of the first film, made of a flexible elastomeric material with a thickness (H) of at most 30 mm and has a continuous cavity.

According to a further advantageous development of the invention, the wound dressing can comprise one or more further flexible films, which are provided for application on the side of the wound dressing that faces away from the wound during use. In such a case, the method described above for a two-ply wound dressing is adapted such that the at least one pocket is applied to that film ply that is present facing away from the wound during use.

A further preferred embodiment of the wound dressing according to the invention comprises at least one pocket which is embodied like a sack or a cone and provided for application to the side of the wound dressing that faces away from the wound during use. Here, the pocket should be applied to the wound dressing such that the opening of the former is present oriented predominantly to the center of the wound dressing. The pocket is preferably made of a film material and should furthermore have a depth a of at most 15 cm, more particularly of at most 10 cm. In particular, the pocket can be attached to the wound dressing by adhesive bonding, thermal welding, pressing or ultrasound welding. The inner surface of the pocket that points toward the wound during use is formed by a first material section of the cone in this embodiment, while the inner surface of the pocket that points away from the wound during use is formed by a second material section of the cone.

The present invention is therefore likewise directed to a method for producing a wound dressing as described above, comprising the following steps:

a) provision of a first flexible film with a first and a second side, with the first side being provided for application on the wound bed, more particularly on exposed internal organs or on the greater omentum, and with the film having at least one opening, b) optional provision of a second flexible film with a first and a second side, with the first side being provided for application on the second side of the first film that faces away from the wound during use, c) optional provision of one or more further flexible films which are provided for application on the side of the wound dressing that faces away from the wound during use, d) provision of at least one pocket embodied in a sack-like or cone-like fashion, in particular a pocket, embodied in a sack-like or cone-like fashion, made of a film material, e) optional connection of the first flexible film to the second flexible film and optional connection of the second flexible film to the one or more further flexible films, and f) application of the at least one pocket embodied in a sack-like or cone-like fashion onto the side of the wound dressing that faces away from the wound during use such that the opening of the pocket predominantly points towards the center of the wound dressing.

Here, according to the invention, there is no conduit present which is applied to the second side of the first film, made of a flexible elastomeric material with a thickness (H) of at most 30 mm and has a continuous cavity. The depth of the at least one pocket is preferably at most 15 cm, more particularly at most 10 cm.

According to a further preferred embodiment, the wound dressing according to the invention comprises at least one pocket, with the pocket being formed by folding back a film portion of the wound dressing. Here, the pocket is more particularly formed by folding back the first film and/or the second flexible film and/or the one or more further flexible films. The following text in an exemplary fashion highlights three possible embodiments i) to iii) for such a pocket which is formed by folding back. The invention is not restricted to the examples proposed here. A multiplicity of further options for implementing the idea of a pocket formed by folding back, illustrated here, emerge for a person skilled in the art.

i) producing a pocket by folding back, with the wound dressing having a circular design and only comprising a single flexible film: At least two radially guided cuts with a depth of approximately 3 cm are introduced into the edge of the first flexible film. The spacing of the cuts on the edge of the film is approximately 5 cm. The section of the first flexible film delimited by the cuts is folded back onto its second side (wound-distant side), with the section being fixed laterally by forming a seam. A pocket produced thus has a depth of approximately 3 cm and a width b of approximately 5 cm, with there being an opening oriented toward the center of the wound dressing.

ii) producing a pocket by folding back, with the wound dressing having a circular design and comprising a second flexible film in addition to a first flexible film: The first film is not cut or folded back. The second flexible film is folded back as described under i) for the first flexible film. In this case, the pocket is formed by the second flexible film. The pocket is arranged situated toward the edge of the wound dressing, with the spacing of the pocket from the edge of the wound dressing being 3 cm.

iii) producing a pocket by folding back, with the wound dressing having a circular design and comprising a further flexible film in addition to a first flexible film and a second flexible film: Three cuts are introduced into the further flexible film such that a rectangularly shaped flap is created, with the outer side of the rectangle having a spacing from the edge of the wound dressing of 5 cm. As a result of folding the flap back towards the interior it is possible to form a pocket, with the folded-back section being fixed on the lateral side by forming a seam.

The present invention is therefore furthermore directed at a method for producing a wound dressing as described above, comprising the following steps:

a) provision of a first flexible film with a first and a second side, with the first side being provided for application on the wound bed, more particularly on exposed internal organs or on the greater omentum, and with the film having at least one opening, b) optional provision of a second flexible film with a first and a second side, with the first side being provided for application on the second side of the first film that faces away from the wound during use, c) optional provision of one or more further flexible films which are provided for application on the side of the wound dressing that faces away from the wound during use, and d) folding back a film portion of the wound dressing, in particular folding back the first film and/or the second flexible film and/or the one or more further flexible films such that at least one pocket is formed, which is predominantly open toward the center of the wound dressing, present on the side of the wound dressing that faces away from the wound during use and simplifies the uniform application and laying out of the wound dressing on the wound bed.

Here, according to the invention, there is no conduit present which is applied to the second side of the first film, made of a flexible elastomeric material with a thickness (H) of at most 30 mm and has a continuous cavity. The depth of the at least one pocket is preferably at most 15 cm, more particularly at most 10 cm.

In order to ensure a sufficient drainage capacity of the wound dressing, provision can optionally be made for the pocket to be made of a material, more particularly a film material, which has a multiplicity of openings distributed across the area. The openings present in the material section provided for forming a pocket should preferably have at least 0.1% and at most 25% of the areal extent, preferably at least 10% and at most 22% of the areal extent of the material section.

In order to apply a wound dressing according to the invention, the user can insert a flat surgical instrument, e.g. a stomach and intestinal spatula, into the at least one pocket and thereupon carefully insert the wound dressing, which is temporarily held on the spatula by the pocket, under the abdominal wall. Alternatively, it would also be possible to insert one or more fingers into the at least one pocket, instead of an instrument, for applying the wound dressing.

In an advantageous development of the invention it is proposed to use a specifically adapted surgical instrument for applying the wound dressing. It was found that an instrument made of a flexible plastic material can be used in a particularly sparing fashion for applying the wound dressing and, in this respect, has advantages over an instrument made of metal. In this context, a flexible plastic material is understood to mean that the Shore A hardness of the material is at most 80, more particularly at most 70 (determined pursuant to DIN 53505 from August 2000, to be precise at 23° C. on a plate-shaped level and flat sample body with a thickness of 6 mm as described in the norm). The instrument has an end piece, which is embodied in a spatula-like manner and can be inserted into a pocket of the wound dressing according to the invention. For safety reasons, the instrument should additionally comprise a means for creating an X-ray contrast such that an instrument left in the wound space can be detected in an X-ray recording. By way of example, the means for creating an X-ray contrast can be an X-ray contrast strip, an X-ray contrast thread or an X-ray contrast chip, which is applied to the instrument. It would also be possible to work a substance that can create an X-ray contrast into the material that is used to produce the spatula.

The invention therefore furthermore relates to a specifically adapted surgical instrument for applying a wound dressing, the wound dressing comprises i) a first flexible film with a first and a second side, with the first side being provided for application on the wound bed, more particularly on exposed internal organs or on the greater omentum, and with the first film furthermore having at least one opening, ii) at least one pocket, which is predominantly open toward the center of the wound dressing, is present on the side of the wound dressing that faces away from the wound during use and simplifies the uniform application and placement of the wound dressing on the wound bed. Here, the surgical instrument has an end piece with a spatula-like design that can be inserted into the pocket of the wound dressing and furthermore comprises a flexible plastic material and a means for creating an X-ray contrast.

The invention likewise relates to the use of a specifically adapted surgical instrument for applying a wound dressing, with the surgical instrument having an end piece, which is embodied in a spatula-like manner and can be inserted into the pocket of the wound dressing, and with the instrument furthermore comprising a flexible plastic material and a means for creating an X-ray contrast. Here, the wound dressing comprises i) a first flexible film with a first and a second side, with the first side being provided for application on the wound bed, more particularly on exposed internal organs or on the greater omentum, and with the first film furthermore having at least one opening, ii) at least one pocket, which is predominantly open toward the center of the wound dressing, is present on the side of the wound dressing that faces away from the wound during use and simplifies the uniform application and placement of the wound dressing on the wound bed.

In practice, it furthermore is found to be very advantageous if the wound dressing additionally comprises one or more liquid-permeable layers for application onto the side of the wound dressing that faces away from the wound (wound-distant side) during use. To the extent that such a liquid-permeable layer is provided, it is thus applied on the wound-distant side on the film ply provided with at least one pocket. As illustrated above, the film ply is the first film, the second film or a further film.

The liquid-permeable layer preferably comprises a porous foam, more particularly a porous polymer foam. An open-cell polymer foam is particularly suitable in this case. Within the scope of this application, the term open-cell means that, compared to the total number of cells, there are at least 60% open cells, preferably at least 90% open cells, more preferably at least 98% open cells, more particularly substantially 100% open cells in the foam (c).

By way of example, suitable materials for a porous foam comprise polyurethane, polyurethane-polyurea copolymers, polyvinyl alcohol (PVA) or silicone.

As an alternative, or in addition thereto, the liquid-permeable layer can comprise textile materials such as wovens or non-wovens, for example a non-woven material of synthetic polymers such as polyamide, polyester or polypropylene.

In the context of the present invention, the porous foams described in the German patent application DE102010034819.8 (not yet published at the time of the present application) can be used in a particularly advantageous fashion to produce the one or more liquid-permeable layers. Reference is herewith made to the content of the German patent application DE102010034819.8. The foams described in DE102010034819.8 do not release foam particles, or only release the latter to a small extent, during the possibly required cutting to size for matching the wound shape. Released foam particles that reach the wound can irritate the wound and have an adverse effect on wound healing.

In particularly advantageous fashion, use can be made of the open-cell polyurethane foam VivanoMed, distributed by the applicant Paul Hartmann AG (Heidenheim, Germany), as a liquid-permeable layer.

The at least one further liquid-permeable layer can improve the softness and tolerance of the wound dressing and can offer an additional contribution to draining wound exudate.

Furthermore, for the purpose of promoting the primary wound closure, it is more particularly very advantageous to apply a porous polymer foam such that the foam is in direct contact with the wound edges.

The at least one further liquid-permeable layer has a thickness of between 2 mm and 50 mm, preferably of between 3 mm and 30 mm.

Here, the further liquid-permeable layer, which preferably comprises a porous polymer foam, can cover the whole area of the film. The liquid-permeable layer is preferably only present on a central portion of the film. Particularly when using the wound dressing as temporary wound closure, it was found to be expedient if a porous polymer foam is applied such that the edges of the foam are in direct contact with the wound edges.

In the context of the present invention, it is also possible for more than one liquid-permeable layer, in particular more than one layer of a porous polymer foam, to be provided on the second side of the wound dressing that faces away from the wound during use. Here, the plurality of layers can have different dimensions and be present in different thicknesses. For negative-pressure therapy of a typical abdominal wound it was found to be advantageous if two layers of an open-cell polyurethane foam with a layer thickness of respectively 16 mm are applied.

The wound dressing according to the invention can furthermore comprise an air-impermeable cover material for airtight closure of the wound and the wound surroundings. Here, "airtight closure" should not be understood to mean that there is no gas exchange between the wound space and the surroundings thereof. Rather, "airtight closure" in this context means that, taking into account the utilized negative-pressure pump, the negative pressure required for the negative-pressure wound therapy can be maintained. It is therefore also possible for use to be made of cover materials which have a small gas permeability, as long as the negative pressure required for the negative-pressure therapy can be maintained.

The cover material is attached in the surroundings of the wound or on the wound edge such that an airtight wound closure is ensured. In the process, it can be expedient if the cover material is equipped to be self-adhesive over the whole area or has a self-adhesive edge. Alternatively, attaching and sealing can for example be brought about using an adhesive film, a liquid adhesive or a sealing compound.

In a preferred embodiment of the invention, the cover material for airtight closure of the wound comprises a water-insoluble polymer or a metal film.

In a particularly preferred embodiment of the invention, the water-insoluble polymer is polyurethane, polyester, polypropylene, polyethylene, polyamide or polyvinyl chloride, polyorganosiloxane (silicone) or a mixture thereof.

It is also possible to use finished products which have the aforementioned properties as cover material. A polyurethane film branded Hydrofilm® (Paul Hartmann AG, Germany) or Visulin® (Paul Hartmann AG, Germany) was found to be a particularly suitable cover material for the device according to the invention.

In the context of the wound dressing according to the invention, a negative-pressure port can furthermore be used for the functional connection of the wound space to a negative-pressure source situated outside of the wound dressing, with the negative-pressure port being designed such that negative pressure can be set in the wound space and liquids can be suctioned out of the wound space. When using the wound dressing in the negative-pressure wound therapy, the negative-pressure port is preferably applied to the side of the air-impermeable cover material that faces away from the wound, with the cover material having suitable openings. A person skilled in the art also knows of negative-pressure ports by the name "port". The negative-pressure port usually comprises a connection line and a negative-pressure adapter in order to be connectible to the further components of the negative-pressure system.

According to a further preferred embodiment, cover material and the means for the functional connection of the wound space to a negative-pressure source situated outside of the cover material are already provided in a ready-made interconnected fashion. It is very particularly preferred for this embodiment to contain a film made of one or more water-insoluble polymers, which has a self-adhesive edge, because this arrangement makes it substantially easier to apply the bandage.

The negative-pressure ports disclosed in the patent applications WO2011091947, WO2011091952 and WO2011076340, as well as in the German patent application DE102011108726.9 (not published at the time of the present application), are particularly suitable for the wound dressing described in the present invention.

According to an alternative embodiment, the functional connection of the wound space to a negative-pressure source situated outside of the cover material can be established using at least one connection line. The at least one connection line can be routed through the cover material or routed under the edge of the cover material. The passage point is to be sealed in an airtight manner in both cases so that the desired negative pressure can be maintained in the bandage. By way of example, an adhesive film, an adhesive compound or an adhesive strip are suitable as a sealing means.

By way of example, the connection line can be a tube, a pipe or another body with a cavity. By way of example, a silicone drainage tube is a suitable tube.

The wound dressing according to the invention can furthermore comprise a means such that the negative pressure actually present within the device can be monitored and set, if required. The means can be in the wound space or at another suitable place.

Alternatively, it is also possible to attach a pressure sensor in the negative-pressure line between wound bandage and the negative-pressure source.

It is envisaged that the aforementioned components are provided to the medical practitioners and specialist staff treating the wound in the form of a ready-made set ("kit"). The invention therefore also relates to a ready-made set for negative-pressure wound treatment, comprising a) a wound dressing according to one or more of claims 1 to 16, b) optionally at least one liquid-permeable layer for application on the second side of the wound dressing that faces away from the wound during use, wherein the at least one liquid-permeable layer preferably comprises one or more areal cushions of a porous polymer foam, more particularly of PU, PVA or silicone, c) an air-impermeable cover material for airtight closure of the wound and the surroundings of the wound, wherein the cover material preferably has an adhesive edge, d) optionally a negative-pressure connection means for the functional connection of the wound space to a negative-pressure source situated outside of the cover material such that negative pressure can be set in the wound space and liquids can be suctioned out of the wound space, wherein the negative-pressure connection means is preferably provided for application to the outer side of the cover material that faces away from the wound during use, and wherein components a) to d) can be present in sterile packaged form.

Negative-pressure ports particularly suitable for the ready-made set are described in the aforementioned patent applications with application numbers WO2011091947, WO2011091952, WO2011076340 and DE102011108726.9 (not published at the time of the present application).

The set can furthermore contain optional components such as e.g. one or more additional areal elements of a liquid-permeable layer, adhesive means for fixing the bandage, sealing means for establishing an air-impermeable seal of the bandage, pressure sensors, connection elements for pressure sensors, tubes, connection pieces for tubes, disinfection means, skin-care products, pharmaceutical preparations or instructions for use. Optionally, one or more stomach and intestinal spatulas conventional in surgery or, alternatively, one or more surgical instruments specifically adapted for applying a wound dressing according to the invention can be added to the set. A surgical instrument specifically adapted for applying a wound dressing according to the invention has an end piece, which is designed like a spatula and can be inserted into the pocket of the wound dressing. The instrument is produced from a flexible plastic material and comprises an X-ray contrast thread.

The set is provided for use with a negative-pressure source. A negative-pressure unit, in particular a portable negative-pressure unit, constitutes a particularly suitable negative-pressure source. A portable negative-pressure unit can contain components such as e.g. a pump, one or more liquid containers, a control unit, a power supply, electric connection means, and tubes. Alternatively, the negative-pressure source can for example be a device for the functional connection of the negative-pressure bandage to an available stationary negative-pressure source.

Portable negative-pressure units particularly suitable for the ready-made set are described in the patent applications WO2011018133 and WO2011018132. A negative-pressure unit particularly suitable for the set is commercially available under the name VivanoTec (producer Paul Hartmann AG, Heidenheim, Germany).

All components for which it is necessary from a medical point of view are preferably made available in sterile packaged form. The advantage of the ready-made set consists of the fact that the negative-pressure bandage can be applied in a quick, standardized and uncomplicated fashion. A further advantage consists of the fact that all components of the set used in the region of the wound can be provided in an already sterilized fashion.

KEY TO THE FIGURES

1. First flexible film
4. Second flexible film
6. Opening in the first flexible film
7. Adhesion or attachment point between first and second film
10. Wound dressing for use in negative-pressure wound therapy, in particular for treatment of abdominal wounds
11. Liquid-permeable layer
12. Interspace between wound bed (e.g. greater omentum or exposed internal organs) and abdominal wall
13. Wound bed (e.g. greater omentum or exposed internal organs)
14. Abdominal wall
15. Wound edge
16. Air-impermeable cover film
17. Opening in the cover film
18. Negative-pressure connection means (port)
19. Negative-pressure line
20. Can for wound exudate
21. Negative-pressure source
25. Pocket open toward the center of the wound dressing
26. Seam or adhesive region between pocket and first or second flexible film
27. Opening in the pocket
28. Adhesive layer for attaching a pocket 40. Device for use in negative-pressure wound therapy, in particular for treatment of abdominal wounds

BRIEF DESCRIPTION OF THE DRAWINGS

In the following text, the wound dressing according to the invention and the device for negative-pressure wound therapy will be explained in more detail on the basis of schematic drawings (not true-to-scale). However, the invention should not be understood as being restricted to the embodiments illustrated in the drawings or in the description of the drawing. Rather, the device according to the invention also comprises combinations of the individual features of the alternative forms.

DETAILED DESCRIPTION OF THE INVENTION

The figures show various embodiments and views of the wound dressing according to the invention which, as a whole, is denoted by reference sign 10.

Figure 1:
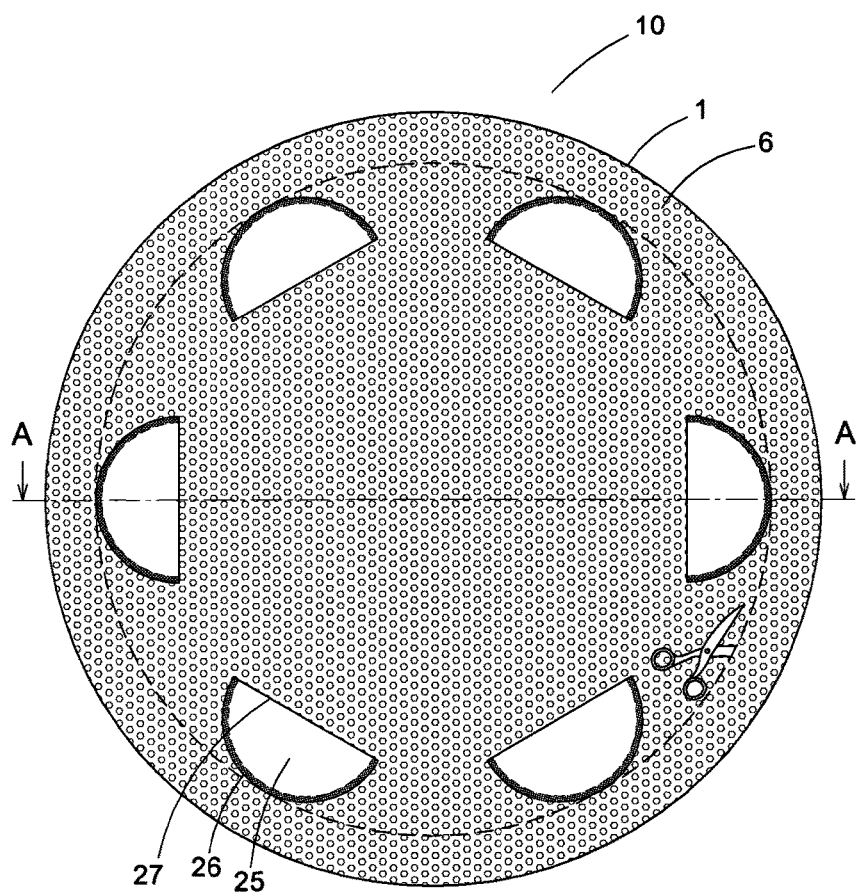
FIG. 1 shows an embodiment of the wound dressing according to the invention for use in negative-pressure therapy, in a plan view of the side of the wound dressing that faces away from the wound. The section shows a magnified view of a pocket with dimensions.
Figure 1:
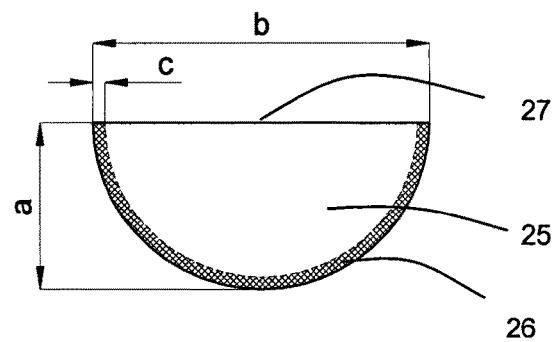

FIG. 1 shows an embodiment which in this case merely comprises a first flexible film 1 in an exemplary manner. The first flexible film 1 has a first side and a second side, wherein the first side is provided for application on the wound bed (see FIG. 7, reference sign 13), in particular on exposed internal organs or on the greater omentum, and hence can serve as wound contact layer and, if need be, as organ screening layer. The flexible film 1 furthermore has a multiplicity of openings 6 which are distributed over the area, with the open area of the openings present in the film being 14%. The openings are circular holes with a diameter of approximately 0.3 mm. According to a further advantageous embodiment which, compared to the aforementioned film 1, is softer and more permeable, the open area of the openings 6 (circular holes with a diameter of 0.3 mm) present in the film 1 is 21%. In general, the sum of the open area of the openings 6 present in the film 1 should be at least 0.1% and at most 25% of the areal extent, preferably at least 10% and at most 22% of the areal extent.

On a circular inner circumference of the film 1, six pockets 25 are arranged on the second side of the first film 1. The pockets are present on approximately 58% of the circle circumference and are distributed on the circumference with regular spacing from one another. The pockets simplify the uniform application and laying out of the wound dressing 10 on the wound bed 13. In the embodiment illustrated in FIG. 1, the pockets have an overall semicircular shape. The pockets are applied to a portion of the wound dressing 10 that is situated toward the edge. The spacing between a pocket 25 and the edge of the wound dressing 10 is 4 cm. The straight side of the semicircle forms an opening 27 that points toward the center of the wound dressing 10 and into which a surgical instrument can be introduced or a finger can be inserted during the application of the wound dressing on the wound bed 13. The pocket 25 is connected to the first film in a non-detachable fashion by means of the seam 26. By way of example, this can be brought about by adhesive bonding or welding. In the example shown in FIG. 1, the pocket 25 is made of an areal material section, for example of a plastic film. The material section forming the pocket 25 can have openings which are distributed over the area of the material section (not illustrated). As a result of this, it is possible to ensure an unchanging permeability for fluid over the area of the wound dressing 10. The width b of the pocket (see magnified section in FIG. 1) is generally at least 1 cm and at most 20 cm, preferably at least 2 cm and at most 10 cm. In the case of the semicircular pockets 25 shown in FIG. 1, the width b is 6 cm for example and the depth a then is 3 cm. The width c of the seam can lie in the region of 0.1 mm to 10 mm.

In one embodiment herein, the opening (27) of the at least one pocket (25) on the uppermost surface is fully exposed to the user and fully accessible by the user.

The scissors symbol in FIG. 1 should indicate that the wound dressing 10 can be adapted to the size required for the treatment of the wound by cutting to size.

If, as in the present example, the wound dressing 10 merely comprises a single flexible film 1, the pockets 25 are applied to the second side of the first film 1. If the wound dressing 10 has a two-ply design, the pockets 25 are generally applied to the second side of the second film. In the case of a wound dressing 10 which moreover comprises additional layers, the pockets 25 are present on the side that faces away from the wound during use of that film ply which is present averted from the wound during use.

Figure 2:
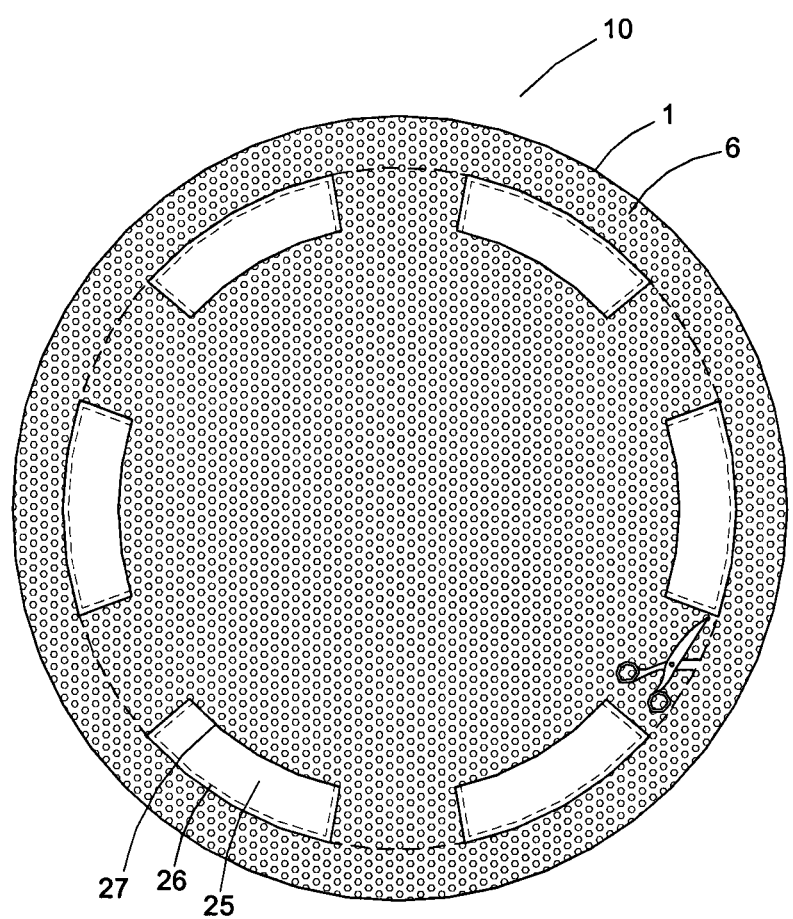
FIG. 2 shows a further embodiment of the wound dressing according to the invention, in a plan view of the side of the wound dressing that faces away from the wound.
Figure 3A:
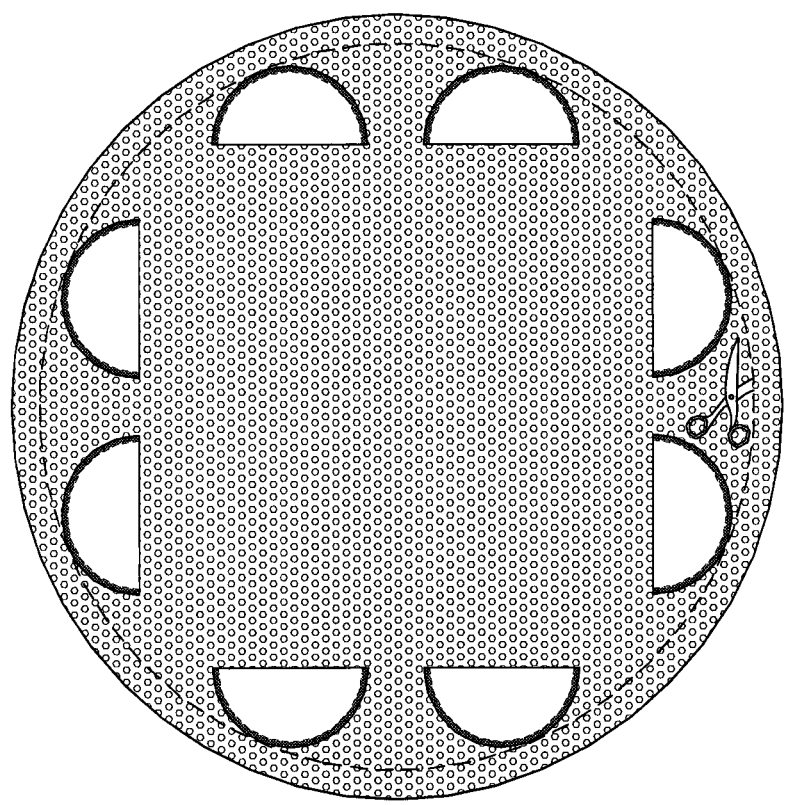
FIGS. 3*a-d* show further exemplary embodiments of the wound dressing according to the invention, in a plan view of the side of the wound dressing that faces away from the wound. The embodiments shown differ in respect of the arrangement of the pockets.
Figure 3B:
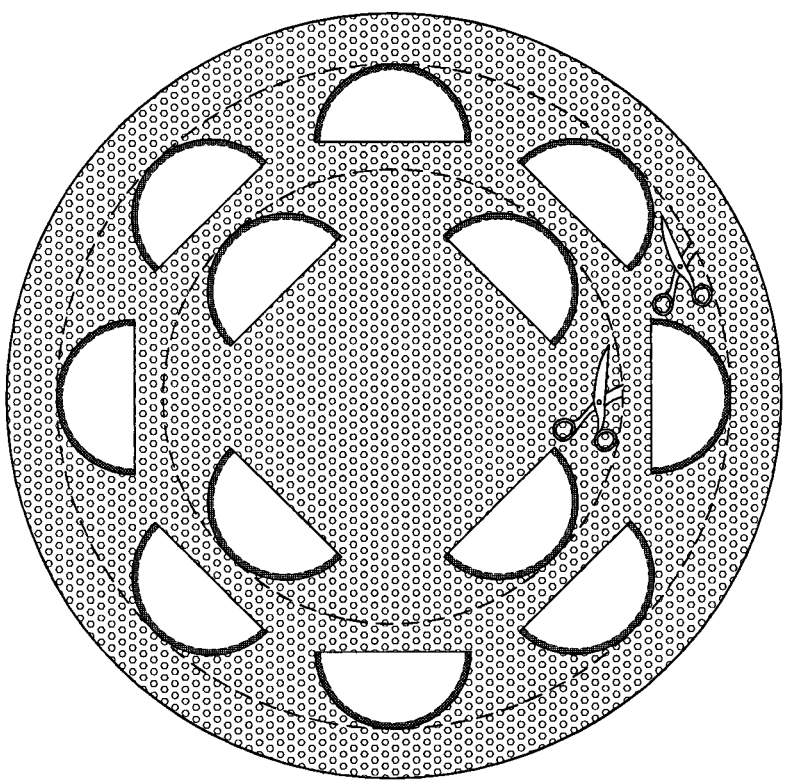
Figure 3C:
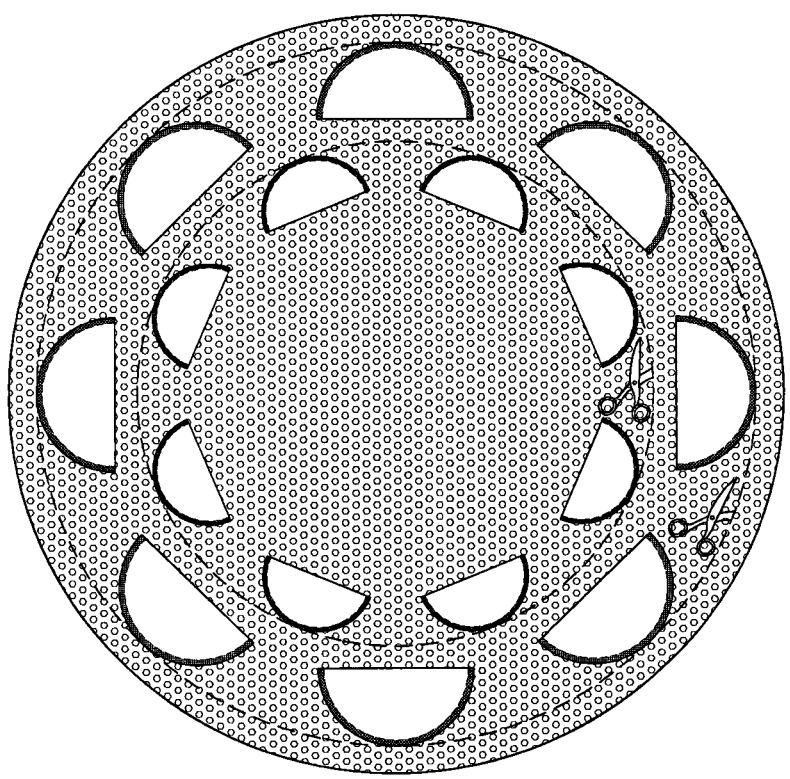
Figure 3D:
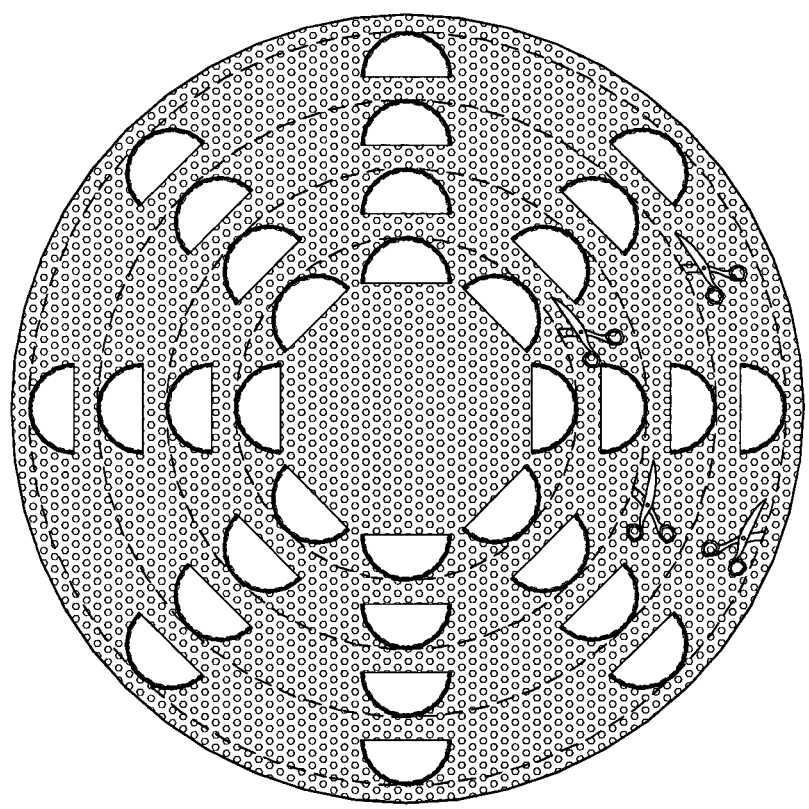

FIG. 2 shows a wound dressing 10 which is otherwise identical to FIG. 1, but differs in respect of the form of the pockets 25. The pockets 25 illustrated schematically in FIG. 2 have the shape of an annular sector. A side of the pocket not connected to the film 1 respectively points toward the center of the wound dressing and forms the opening which is provided for the insertion of a surgical instrument or a finger. The three further sides of the annular sector are connected in a non-detachable fashion to the film by means of a seam. As in the case of the pockets 25 in FIG. 1, the pockets are produced by the application of an areal material section onto a first flexible film.

FIGS. 3 *a* to 3*d* illustrate further advantageous examples for arranging the pockets 25 on the side of the wound dressing 10 that faces away from the wound during use. The wound dressing illustrated in FIG. 3a comprises eight semicircular pockets, the open sides of which are aligned with respect to a square centered around the center of the wound dressing and predominantly point toward the center of the wound dressing. FIG. 3b shows an exemplary embodiment which has an arrangement of the pockets 25 on two concentric circle circumferences. Such an arrangement is particularly advantageous because, even after cutting an edge region of the wound dressing 10 to size for the purpose of adapting the size of the wound dressing, intact pockets situated further inward are still present (inner circle of pockets), while the pockets arranged further outward were possibly destroyed by the cutting to size. It is possible to identify from FIG. 3c that the wound dressing can comprise pockets of different sizes. In the case of an embodiment already shown in FIG. 3b, comprising two concentric rings of pockets, the pockets arranged closer to the center of the wound dressing could for example have a smaller design, as illustrated schematically in FIG. 3c. As a development of this idea, it is proposed to arrange the pockets in a multiplicity of concentric rings around the center of the wound dressing 10 in order to further improve the possibility of cutting to size. Such an example with four rings of pockets arranged concentrically on the wound dressing is shown in FIG. 3d in an exemplary fashion. In such a case, the pockets must overall have a smaller design, for example with a width b of 3 cm and a depth a of 1.5 cm.

Figure 4:
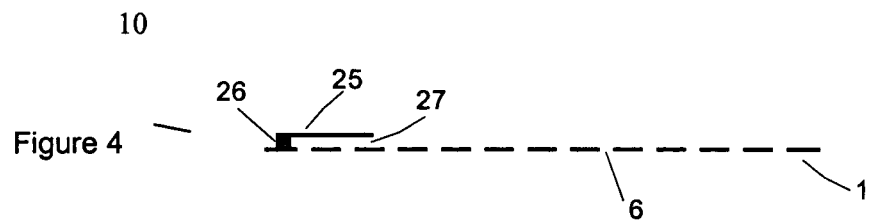
FIG. 4 shows a cross section of a section of the single-ply wound dressing illustrated in FIG. 1, corresponding to the line A-A in FIG. 1.

What is shown in FIG. 4 is a cross section corresponding to the line A-A in FIG. 1 of a section of the embodiment of the wound dressing 10 according to the invention illustrated in FIG. 1. A first flexible film 1 with openings 6 can be identified in FIG. 4. An areal material section was applied to the second side of the film 1 for forming a pocket 25. The material section is attached in a non-detachable fashion to the first film 1 by means of the arc-shaped seam 26 (see FIG. 1). Opening 27 points to the center of the wound dressing. According to an advantageous development of the invention, the first film 1 has openings 6 that are conical or cylindrical to the greatest possible extent and have a three-dimensional shape (not illustrated in FIG. 4) and so, as a result of this, the film has a rough and a smooth side. Here, the smooth side should preferably form the first side of the film 1, i.e. be provided as wound-contact layer.

Figure 5:
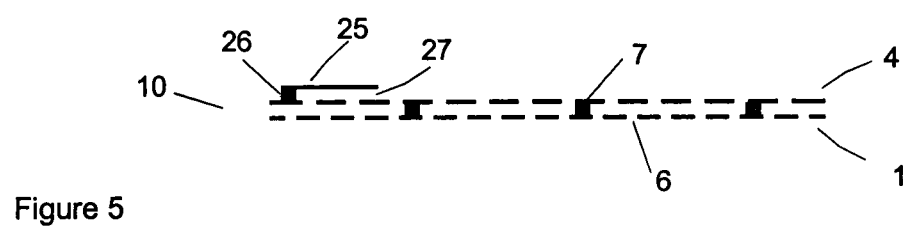
FIG. 5 shows a cross section of a further embodiment of the wound dressing with two film plies. The cut was made through the center of the wound dressing.

FIG. 5 shows, in a very schematic illustration, a wound dressing 10 according to the invention, which comprises a second flexible film 4 in addition to a first flexible film 1.

Analogously to the embodiment illustrated in FIG. 4, an areal material section was applied to form a pocket 25 by means of a seam 26 (see FIG. 1), wherein, however, the material section is present on the second side of the second film 4. First and second film (1; 4) are interconnected by adhesion points 7. By way of example, adhesion points 7 can be created by punctiform adhesive bonding or punctiform welding between first and second film. In the case of such a two-ply embodiment of the wound dressing, a labyrinth-like inner cavity, which can promote a distribution of the negative pressure in the wound space, is formed by the first film 1 and the second film 4. This effect can be further amplified if material with a strength of e.g. 0.1 mm to 3 mm is applied at the adhesion points 7 such that there are spacers present between first and second film. According to a particularly advantageous development of the invention, both the first film 1 and the second film 4 has openings 6 that are conical or cylindrical to the greatest possible extent and have a three-dimensional shape (not illustrated in FIG. 5) such that, as described above in the context of FIG. 4, each of the two films has a smooth side and a roughened side that is opposite to the smooth side. It is now proposed that the rough sides of first film 1 and second film 4 are brought into mutual contact. A cavity formed by first film 1 and second film 4 is created, wherein the three-dimensionally shaped openings bring about a spacing. Such a cavity formed by three-dimensional structures largely remains even during the negative-pressure treatment and promotes both the distribution of the negative pressure in the wound space and the drainage of wound exudate to the negative-pressure source.

Figure 6:
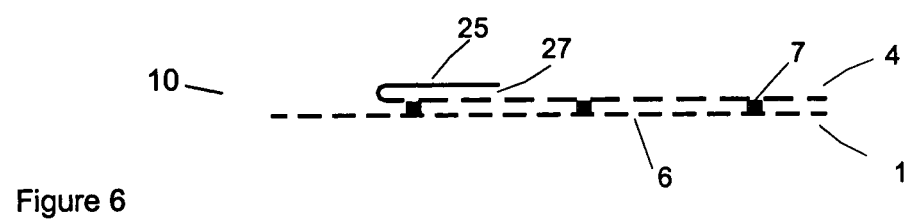
FIG. 6 shows a cross section of a further embodiment of the wound dressing with two film plies. The embodiment differs from the embodiment shown in FIG. 5 by means of the pockets. The cut was made through the center of the wound dressing.

FIG. 6 should, in an exemplary fashion, illustrate an alternative embodiment of the pocket 25. It is possible to identify a wound dressing 10 according to the invention, comprising a first flexible film 1 and a second flexible film 4, wherein the film plies are present interconnected in a non-detachable fashion by means of adhesion points 7. A labyrinth-like interspace is formed between first film 1 and second film 4. According to the embodiment of the invention shown in FIG. 6, a pocket 25 is formed by folding back the second film 4. In order to produce a pocket 25 formed by folding back, at least two radially guided cuts with a depth of approximately 3 cm are introduced into the edge of the second flexible film. A multiplicity of such cuts are preferably made at regular spacings around the complete edge of the second film. The spacing of the cuts on the edge of the film can for example be approximately 5 cm. A section of the second film 4 flanked by two cuts is then folded back onto its second side (wound-distant side), with the section being fixed laterally by forming a seam (not visible in FIG. 6). A pocket produced thus has an opening oriented toward the center of the wound dressing. According to a simpler embodiment (not illustrated) of the wound dressing 10 according to the invention, the wound dressing merely comprises a single flexible film 1, with the at least one pocket being formed by folding back the first flexible film 1. In the case of a wound dressing with a two-ply design, it would also be feasible that first film 1 and second film 4 are folded back at the same time in order to form a pocket (not illustrated).

Figure 7:
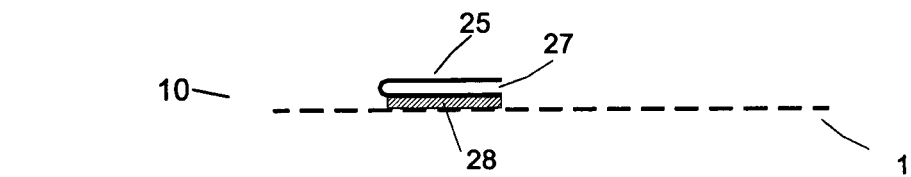
FIG. 7 shows a further embodiment of the wound dressing with one film ply and a pocket embodied like a cone. The cut was made through the center of the wound dressing.

A further advantageous embodiment of a wound dressing 10 according to the invention is presented in FIG. 7. In place of an areal material section (see FIGS. 4; 5), at least one material section with a cone-like design, in particular a film section with a cone-like design, is applied in a non-detachable fashion to the side of the wound dressing that faces away from the wound during use by means of an adhesive layer 28. In the embodiment shown in FIG. 8 in an exemplary fashion, a complete pocket 25 is present on a first flexible film 1. The opening 27 of the cone points toward the center of the wound dressing 10. A pocket with a cone-like shape could likewise be applied to the second side of a second flexible film (not illustrated in FIG. 8) or on the side of one or more further film plies that faces away from the wound during use.

Figure 8:
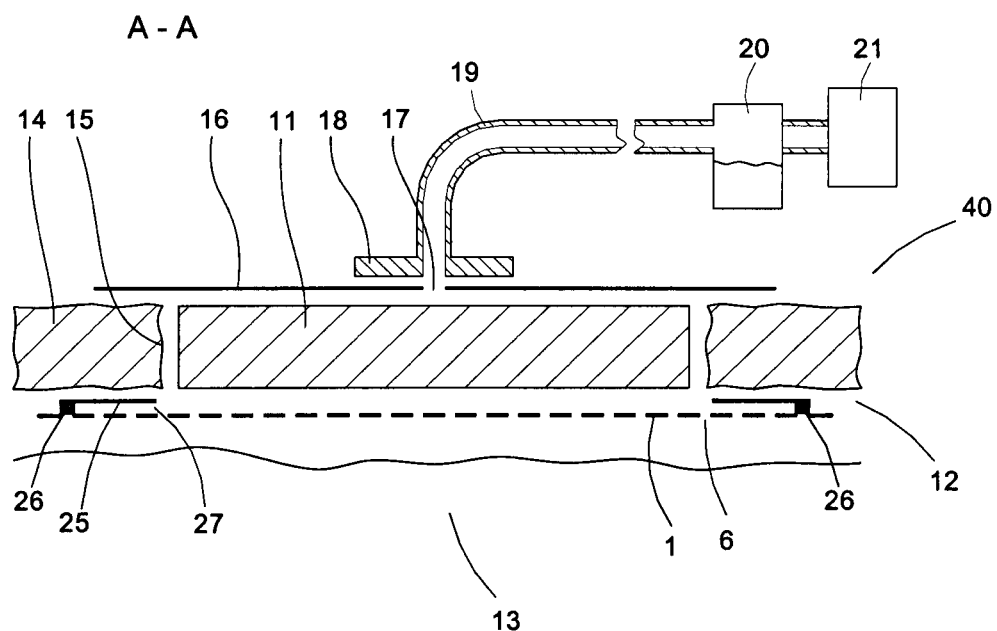
FIG. 8 shows, in a cross section, a device applied to an abdominal wound, for use in negative-pressure wound therapy. The wound dressing comprised by the device has the design shown in FIG. 1 and FIG. 4. The cut was made through the center of the wound dressing, corresponding to the line A-A in FIG. 1.

FIG. 8 shows, in a very schematic illustration, a device 40, applied to an abdominal wound, for negative-pressure wound therapy. The device comprises a wound dressing 10 according to the invention, as explained in more detail above, with first film 1 and pockets 25 which simplify the uniform application and laying out of the wound dressing 10 on the wound bed 13. The first side of the first film 1 is applied to the wound bed 13, in particular to exposed internal organs or to the greater omentum. First film 1 and the pockets 25 applied thereon are usually inserted into the interspace 12 formed between wound bed 13 and abdominal wall 14. Inserting the wound dressing into the interspace 12 formed between wound bed 13 and abdominal wall 14 is simplified by the pockets 25 which are open toward the center of the wound dressing because the treating medical practitioner can insert a stomach or intestinal spatula or, optionally, a finger into the pockets and thereupon introduce the edge region of the wound dressing between abdominal wall 14 and the wound bed 13.

On the side of the wound dressing that faces away from the wound during use there is a liquid-permeable layer 11, which more particularly is a porous polymer foam. Use is preferably made of an open-cell polyurethane foam. Depending on the depth of the wound, it is possible for a plurality of layers of the liquid-permeable layer 11 to be present (not illustrated). By cutting to size, the liquid-permeable layer 11 was matched to the size of the wound such that the edge of the liquid-permeable layer 11 is in direct contact with the wound edge 15. It is known that contacting the wound edge 15 with a porous polymer foam 11 promotes the growth of the wound-edge tissue. The device 40 furthermore comprises an air-impermeable cover material 16 for airtight closure of the wound, and also a negative-pressure port 18 (port), that is applied onto the air-impermeable cover material 16 on the side that faces away from the wound, for the functional connection of the wound space to a negative-pressure source 21 situated outside of the cover material 16. The negative-pressure port 18 is attached in the region of an opening 17 introduced into the air-impermeable cover material 16. When the negative-pressure source 21 (e.g. a negative-pressure pump), which is connected in fluid-conducting fashion to the port 18 via a collection can for wound exudate 20 and a negative-pressure line 19, is in operation, negative pressure can be set in the wound space and liquids can be suctioned out of the wound space. Wound exudate suctioned out of the wound space via the negative-pressure line 19 is collected in the can 20. A filter (not illustrated) is expediently provided between can 20 and negative-pressure source 21. When negative pressure is applied, it is possible for wound exudate from the wound bed 13 to reach the liquid-permeable layer 11 via openings 6 in the first film 1. From the liquid-permeable layer 11, the fluid is transported away through an opening 17 in the cover film 16 to the negative-pressure port 18 and on to the can 20 through the negative-pressure line 19.

Application of the Wound Dressing

During the application for negative-pressure therapy of large-area wounds in the abdominal region, the wound dressing 10 according to the invention is first of all placed on the portion of the wound bed 13 accessible to the user. The edge of the wound dressing 10 is then, with the aid of the at least one pocket present on the wound dressing, inserted approximately 1 to 15 cm deep into the interspace formed by abdominal wall 14 and wound bed 13. The wound dressing therefore forms a screening layer, which is permeable to wound fluid, for the exposed internal organs. One or more liquid-permeable layers 11, in particular layers made of a porous polymer foam, are preferably applied to the screening layer formed by one or more films. Here, wound healing is greatly promoted if the liquid-permeable layer 11 is matched to the shape of the wound such that the wound edges 15 are in complete contact with the one or more liquid-permeable layers 11.

For the purpose of airtight closure of the wound region, an air-impermeable cover material 16 is placed over the wound. The edges of the cover material 16 are adhesively bonded to the intact skin. Moreover, a sub-closure port 18 is attached in order to establish a functional connection of the wound space to a negative-pressure source 21, e.g. a negative-pressure pump, situated outside of the cover material 16 such that negative pressure can be set in the wound space and liquids can be suctioned out of the wound space. The negative-pressure port 18 is preferably adhesively bonded onto the outer side of the cover material 16 that faces away from the wound, with a suitable opening 17 being cut into the otherwise air-impermeable cover material 16 prior to the adhesive bonding. The negative-pressure therapy is initiated by connecting the negative-pressure port 18 to a negative-pressure source 21 and by applying a preferably constant negative pressure for a period of a few minutes up to a number of days.

A preferred negative pressure is in the region from at least 80 mm Hg to at most 250 mm Hg, preferably 125 mm Hg.

Accordingly, the present invention describes a method for negative-pressure wound therapy, in particular for a wound in the abdominal region, which method comprises the following steps:

a) applying a wound dressing according to the invention according to one of claims 1 to 17 on the wound bed, in particular on exposed internal organs or on the greater omentum, b) sealing the wound using a suitable airtight cover 16, c) optional attaching of a negative-pressure connection means 18, d) establishing a fluid communication with a negative-pressure source, e) applying negative pressure for at least 30 minutes and for at most 5 days.

What is claimed is:

1. A wound dressing (10) for use in negative-pressure wound therapy, in treatment of abdominal wounds, comprising:
   i) a first flexible film (1) that forms a planar surface having a first and a second side, with the first side being provided for application on a wound bed (13), and with the first flexible film (1) furthermore having a multiplicity of openings (6) distributed evenly across the first flexible film (1) and which are capable of enabling fluid communication through the first flexible film (1); and
   ii) at least three pockets (25), each of the at least three pockets include an opening (27) that predominantly is directed toward a center of the wound dressing (10), the at least three pockets (25) and the openings (27) are present on and above an uppermost surface of the first flexible film (1) that faces away from a wound during use and simplifies a uniform application and placement of the wound dressing (10) on the wound bed (13),
   wherein there is no additional conduit on the second side of the first flexible film (1).

2. The wound dressing (10) according to claim 1, wherein the openings (6) present in the first flexible film (1) have a three-dimensional shape that is conical or cylindrical to the greatest possible extent and, as a result of this, the film (1) has a smooth side and a roughened side opposite to the smooth side.

3. The wound dressing (10) according to claim 2, wherein the the smooth side of the first film (1) is the side that is configured to face the wound, and the side of the first film (1) configured to face away from the wound during use is formed by the roughened side.

4. The wound dressing (10) according to claim 1, wherein the openings (27) of the at least three pockets (25) form a conical shape.

5. The wound dressing (10) according to claim 1, wherein the at least three pockets (25) are formed by adhesive bonding, thermal welding, pressing or ultrasound welding, of an areal material section on the side of the wound dressing (10) that faces away from the wound during use.

6. The wound dressing (10) according to claim 1, wherein the at least three pockets (25) are present on the second side of the first flexible film (1) such that the openings (27) of the at least three pockets (25) on the uppermost surface are capable of being fully exposed to the user and fully accessible by the user.

7. The wound dressing (10) according to claim 1, wherein the first flexible film (1) comprises two or more separate films applied together.

8. The wound dressing (10) according to one of claim 1, wherein the at least three pockets are formed by folding back a film portion of the wound dressing.

9. The wound dressing (10) according to claim 1, wherein the sum of the open area of the openings (6) present in the first flexible film (1) is at least 0.1% and at most 25% of an areal extent of the first flexible film (1).

10. The wound dressing (10) according to claim 1, wherein the pockets (25) are arranged on one or more concentric circles which encircle the center point of the wound dressing and wherein the pockets are present on each circle distributed with a uniform spacing between one another.

11. The wound dressing (10) of claim 1, wherein the multiplicity of openings (6) is present in an amount of from −150 to 190 openings per $cm^2$ or 260 to 300 openings per $cm^2$.

12. The wound dressing (10) of claim 1, wherein the multiplicity of openings (6) are holes wherein the sum of the area of the holes is at least 0.5% and at most 25% of an areal extent of the first flexible film (1).

13. The wound dressing (10) according to claim 1, wherein the at least three pockets (25) substantially have a form of a rectangle, a trapezium, a semi-circle, a triangle, an annulus or an annular sector.

14. The wound dressing (10) according to claim 1, furthermore comprising one or more liquid-permeable layers (11) fabricated from a porous polymer foam, for application on the side of the wound dressing (10) that faces away from the wound during use.

15. The wound dressing (10) of claim 1 wherein the wound bed (13) is exposed internal organs or a greater omentum.

16. The wound dressing (10) of claim 1 wherein the at least three pockets (25) are situated at or adjacent to a peripheral edge of the wound dressing.

17. The wound dressing (10) of claim 1 which further comprises a negative pressure port and/or functional connection to a negative pressure source.

18. The wound dressing (10) of claim 1 wherein the at least one pocket (25) has a lateral seam.

19. The wound dressing (10) of claim 1, wherein the at least three pockets (25) are uniformly spaced from each other on the planar surface of the first flexible film (1) that is configured to face away from the wound, and are symmetrically placed on the wound dressing (10).

20. A device (40) for use in negative-pressure wound therapy, for treatment of abdominal wounds, comprising:
  a) a wound dressing (10) which includes:
    i) a first flexible film (1) that forms a planar surface having a first and a second side, with the first side being provided for application on a wound bed (13), and with the first flexible film (1) furthermore having a multiplicity of openings (6) distributed evenly across the first flexible film (1) and which are capable of enabling fluid communication through the first flexible film (1); and
    ii) at least three pockets (25), which include an opening (27) that predominantly is directed toward a center of the wound dressing (10), the at least three pockets (25) and the openings (27) are present on and opened above an uppermost surface-of the first flexible film (1) that faces away from a wound during use and simplifies the uniform application and placement of the wound dressing (10) on the wound bed (13), characterized in that there is no additional conduit present which is applied to the second side of the first film (1); and
  b) an airtight cover material (16) for air-impermeable closure of a wound and wound surroundings, which air-impermeable enclosure provides a wound space formed thereby, and a negative-pressure port, which can be applied to the air-tight cover material (16) on a side that faces away from the wound, for a functional connection of the wound space to a negative-pressure source (21) situated outside of the airtight cover material (16) such that negative pressure can be set in the wound space and liquids can be suctioned out of the wound space.

21. The device (40) of claim 20 wherein the wound bed (13) is exposed internal organs or a greater omentum.

* * * * *